(12) United States Patent
Unger et al.

(10) Patent No.: US 12,226,286 B2
(45) Date of Patent: *Feb. 18, 2025

(54) TWO-WAY RADIO DEVICE FOR HEARING PROTECTION DEVICES

(71) Applicant: Good Sportsman Marketing, LLC, Irving, TX (US)

(72) Inventors: Howard Unger, Henderson, NV (US); Daniel Dvorak, Henderson, NV (US)

(73) Assignee: GOOD SPORTSMAN MARKETING, LLC, Irving, TX (US)

(*) Notice: Subject to any disclaimer, the term of this patent is extended or adjusted under 35 U.S.C. 154(b) by 238 days.

This patent is subject to a terminal disclaimer.

(21) Appl. No.: 17/949,110

(22) Filed: Sep. 20, 2022

(65) Prior Publication Data
US 2023/0057114 A1 Feb. 23, 2023

Related U.S. Application Data

(63) Continuation-in-part of application No. 16/530,722, filed on Aug. 2, 2019, now Pat. No. 11,451,900.

(60) Provisional application No. 62/717,809, filed on Aug. 11, 2018.

(51) Int. Cl.
*A61F 11/14* (2006.01)
*H04R 1/10* (2006.01)

(52) U.S. Cl.
CPC ............ *A61F 11/14* (2013.01); *H04R 1/1083* (2013.01)

(58) Field of Classification Search
CPC .. H04R 1/1075; H04R 1/1008; H04R 1/1083; H04R 1/1066; H01Q 1/273; A61F 11/14; A61F 2011/145

USPC .................................................. 381/74, 371
See application file for complete search history.

(56) References Cited

U.S. PATENT DOCUMENTS

| | | |
|---|---|---|
| 2,235,372 A | 3/1941 | Kalbitz |
| 3,306,991 A | 2/1967 | Wood |
| 4,905,322 A | 3/1990 | Aileo et al. |
| 5,469,505 A | 11/1995 | Gattey et al. |
| 5,835,609 A | 11/1998 | LeGette et al. |
| 5,862,241 A | 1/1999 | Nelson |
| 6,430,299 B1 | 8/2002 | Hall et al. |
| 7,171,698 B2 | 2/2007 | Saffran |
| 8,213,667 B2 | 7/2012 | Nelson et al. |
| 8,488,814 B2 | 7/2013 | Robuchon et al. |
| 9,445,182 B2 | 9/2016 | Pizzaro et al. |
| 9,641,926 B2 | 5/2017 | Awiszus et al. |
| 10,154,335 B1 | 12/2018 | Hoang |

(Continued)

FOREIGN PATENT DOCUMENTS

| | | |
|---|---|---|
| CN | 214967652 U | 12/2021 |
| CN | 114564103 A | 5/2022 |

(Continued)

*Primary Examiner* — Paul Kim
*Assistant Examiner* — Douglas J Suthers
(74) *Attorney, Agent, or Firm* — Cabello Hall Zinda, PLLC

(57) ABSTRACT

A two-way radio device for hearing protection devices provides communication capabilities to users wearing hearing protection devices, which would ordinarily hinder or block communication. The two-way radio device removably attaches to a portion of a hearing protection device and connects to the speakers thereof. One or more wireless transceivers provide wireless transmission of audio between users of hearing protection devices enhanced with the two-way radio device. Users remain protected by their hearing protection devices and while communicating freely in high decibel environments.

28 Claims, 7 Drawing Sheets

(56) References Cited

U.S. PATENT DOCUMENTS

| | | |
|---|---|---|
| 10,567,860 B2 | 2/2020 | Han |
| 10,779,071 B2 | 9/2020 | Wu |
| 11,477,575 B2 | 10/2022 | Degner et al. |
| 11,736,855 B1 | 8/2023 | Xu |
| 2009/0323975 A1 | 12/2009 | Groesch |
| 2011/0026726 A1 | 2/2011 | Kuo |
| 2011/0051976 A1 | 3/2011 | Tsai |
| 2014/0321658 A1 | 10/2014 | Rahangdale |
| 2018/0176673 A1 | 6/2018 | Madsen et al. |
| 2018/0338201 A1 | 11/2018 | Mann |
| 2021/0260414 A1 | 8/2021 | Mundy et al. |
| 2022/0353596 A1 | 11/2022 | Kuraoka et al. |

FOREIGN PATENT DOCUMENTS

| | | |
|---|---|---|
| EP | 3337181 A1 | 6/2018 |
| GB | 1376455 A | 12/1974 |
| GB | 2586915 A | 3/2021 |
| WO | 9530221 A1 | 11/1995 |
| WO | 2008122081 A1 | 10/2008 |

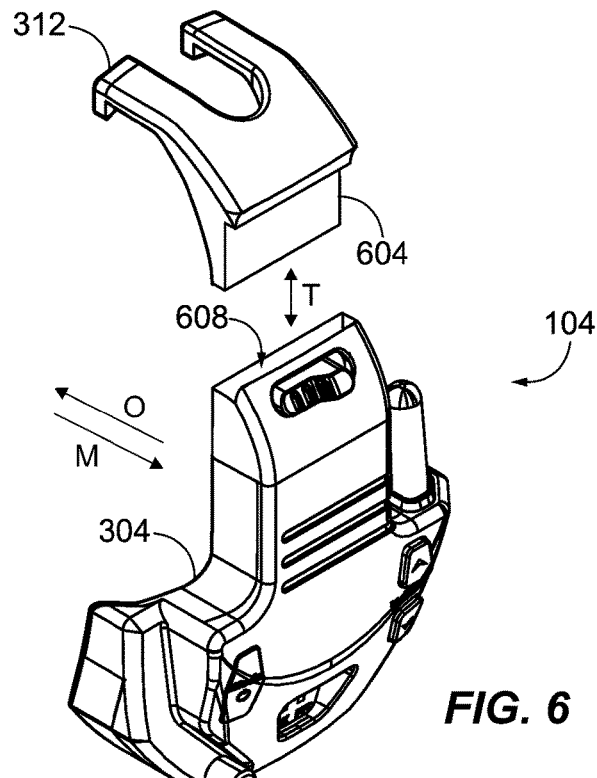
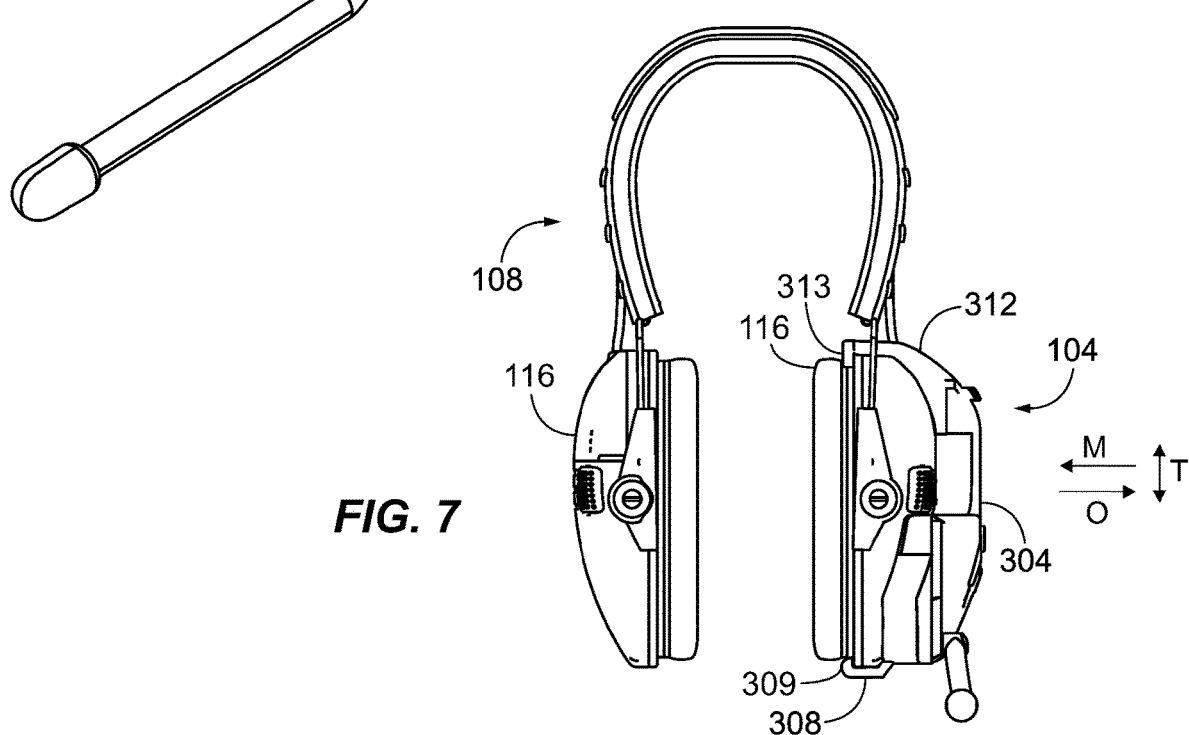
FIG. 6
FIG. 7

TWO-WAY RADIO DEVICE FOR HEARING PROTECTION DEVICES

CROSS-REFERENCE TO RELATED APPLICATION

This application is a continuation-in-part of U.S. patent application Ser. No. 16/530,722, filed Aug. 2, 2019, which claims priority to U.S. Provisional Patent Application No. 62/717,809, filed Aug. 11, 2018.

BACKGROUND OF THE INVENTION

Field of the Invention

The invention relates to communication transceivers and in particular to a two-way radio device for hearing protection devices.

Related Art

Personal protective equipment, such as earmuffs or earplugs, are recommended for use in environments where people are exposed to harmful or potentially harmful decibel levels. In general, this equipment protects users by providing a barrier which reduces the level of noise or other sounds that is able to reach the users' ears. For instance, sound may be attenuated by covering the entire ear or by an insert placed in the ear canal.

From the discussion that follows, it will become apparent that the present invention addresses the deficiencies associated with the prior art while providing numerous additional advantages and benefits not contemplated or possible with prior art constructions.

SUMMARY OF THE INVENTION

A two-way radio device for hearing protection devices is disclosed herein. As will be described further below, the two-way radio device allows a user to communicate while being protected by a hearing protection device that would ordinarily hinder or block audible communication. In this manner, a user can remain protected while also communicating freely with other users even in a high decibel environment. In addition, the two-way radio device enhances communication by permitting users to communicate over extended distances.

Various embodiments of a two-way radio device for hearing protection devices are disclosed herein. In one exemplary embodiment, a two-way radio device is provided for a hearing protection device comprising one or more cups having one or more speakers and an audio input.

The two-way radio device itself comprises an enclosure shaped to receive at least a portion of at least one of the cups, a microphone that captures audio, and a radio transceiver that wirelessly transmits the audio captured by the microphone to a remote two-way radio and wirelessly receives one or more wireless signals from the remote two-way radio. An audio output connects to the audio input of the hearing protection device such that audio carried by the wireless signals is transmitted to the speakers via the audio output. The two-way radio device is removably secured to the hearing protection device via the enclosure.

The enclosure may receive at least a portion of a cup at its back end, such as within one or more compartments at the back end of the enclosure. In addition, the enclosure may comprise one or more mating surfaces corresponding to one or more contours of the portion of the cup. This portion of the cup may be nested within the enclosure when the two-way radio device is secured to the hearing protection device as well.

An additional connector that is aligned such that the additional connector physically connects to the hearing protection device when the two-way radio device is secured a cup may be provided as well. One or more signals other than audio may be communicated between the two-way radio device and the hearing protection device via the additional connector.

In another exemplary embodiment, a two-way radio device is provided for a hearing protection device comprising one or more speakers and an audio input. The two-way radio device itself comprises an enclosure shaped to receive a portion of the hearing protection device, a microphone that captures audio, and a radio transceiver that wirelessly transmits the audio captured by the microphone to a remote two-way radio and wirelessly receives one or more wireless signals from the remote two-way radio. An audio output connects to the audio input of the hearing protection device such that audio carried by the wireless signals is transmitted to the speakers via the audio output. The two-way radio device is removably secured to the hearing protection device via the enclosure.

Similar to above, the enclosure may be shaped to receive the portion of the hearing protection device at its back end, such as within one or more compartments at the back end of the enclosure. The hearing protection device may be nested within the enclosure when the two-way radio device is secured to the hearing protection device. One or more mating surfaces corresponding to one or more contours of the portion of the hearing protection device may be provided as well.

An additional connector can be aligned such that the additional connector physically connects to the hearing protection device when the two-way radio device is secured to the portion of the hearing protection device. One or more signals other than audio may be communicated between the two-way radio device and the hearing protection device via the additional connector.

Various methods are disclosed herein as well. For example, in one embodiment a method of improving a hearing protection device is provided for a hearing protection device comprising one or more speakers and an audio input.

The method itself comprises providing a two-way radio device comprising an enclosure shaped to receive a portion of the hearing protection device, a microphone that captures audio, a radio transceiver, and an audio output. The two-way radio device is removably secured to the hearing protection device via the enclosure.

Audio captured by the microphone is wirelessly transmitted to a remote two-way radio via the radio transceiver, and one or more wireless signals from the remote two-way radio is wirelessly received via the radio transceiver. Audio from the wireless signals is transmitted to the speakers of the hearing protection device via the audio output.

The enclosure may be shaped to receive the portion of the hearing protection device at its back end, such as within one or more compartments at the back end of the enclosure. The portion of the hearing protection device may be nested within the enclosure when the two-way radio device is secured to the hearing protection device. The enclosure may comprise one or more mating surfaces corresponding to one or more contours of the portion of the hearing protection device as well. In addition, at least two seals may be provided at a cup of the hearing protection device.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

FIG. 6 is a perspective view of an exemplary communication device;

FIG. 7 is a side view of an exemplary communication device attached to a hearing protection device;

DETAILED DESCRIPTION OF THE INVENTION

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

It is often difficult to communicate when hearing protection devices are adorned. Users often resort to raising their voices or partially or completely removing their hearing protection in order to communicate with other people. This is inconvenient and undesirable in terms of hearing protection. Moreover, vocal communication is limited to the range a user's voice or other audible communication can travel.

In general, the communication device herein adds communication capabilities to hearing protection devices. This permits users to communicate with one another while remaining protected from hazardous sound levels. The communication device also enhances communication by extending the range within which users can communicate. Moreover, the communication device is unobtrusive and can be conveniently used during work, outdoor activity, or other physical activity. The communication device will be first described in connection with a hearing protection device, such as shown in FIGS. 1 and 2.

Figure 1:
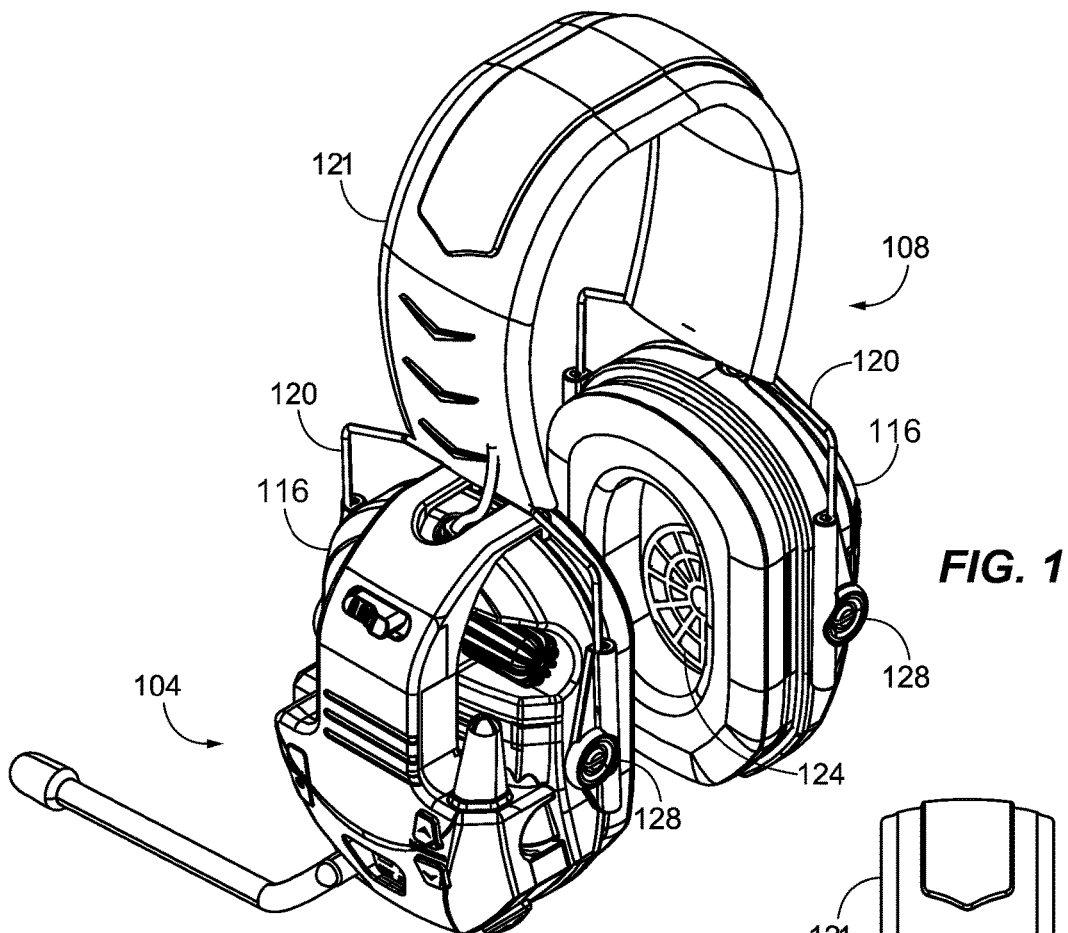
FIG. 1 is a perspective view of an exemplary communication device attached to a hearing protection device.
Figure 2:
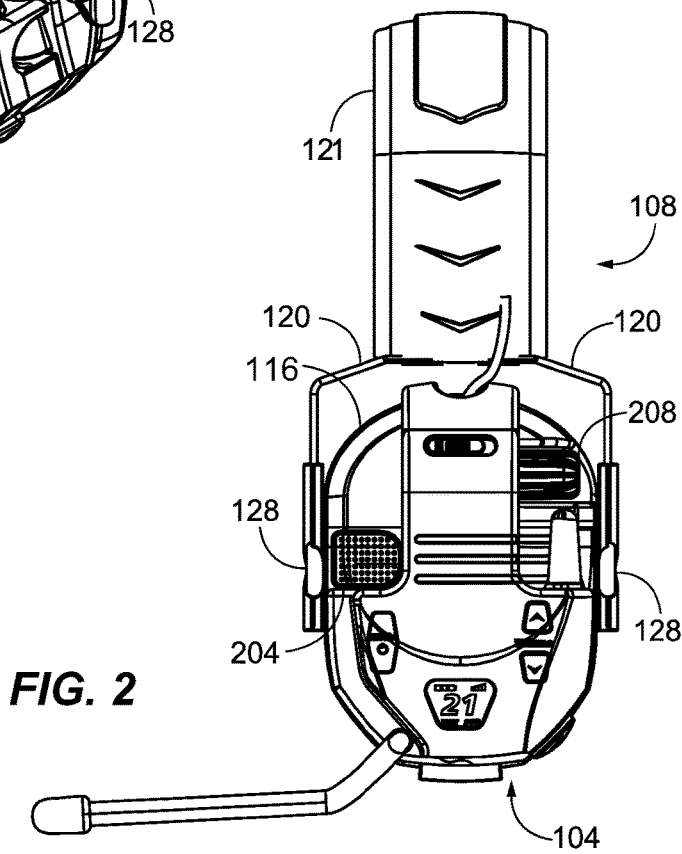
FIG. 2 is a side view of an exemplary communication device attached to a hearing protection device.

FIG. 1 illustrates an exemplary communication device 104, which is an independent device, that has been attached to a hearing protection device 108 for use. As can be seen, a hearing protection device 108 may comprise an earmuff comprising a headband 112 and cups 116 that cover a user's ears. The cups 116 may be pivotally attached to the headband 112 by one or more pivoting mounts 128. In some embodiments, a pivoting mount 128 may comprise one or more arms 120.

The exemplary hearing protection device 108 of FIG. 1 features active noise cancellation via a speaker 124 in each of the cups 116. As shown in FIG. 2, a hearing protection device 108 may comprise one or more microphones 204 for active noise cancellation as well. In addition, one or more controls 208 may be provided, such as to adjust the volume at the speakers 124, turn on/off active noise cancellation, or control other functions of the hearing protection device.

Figure 3:
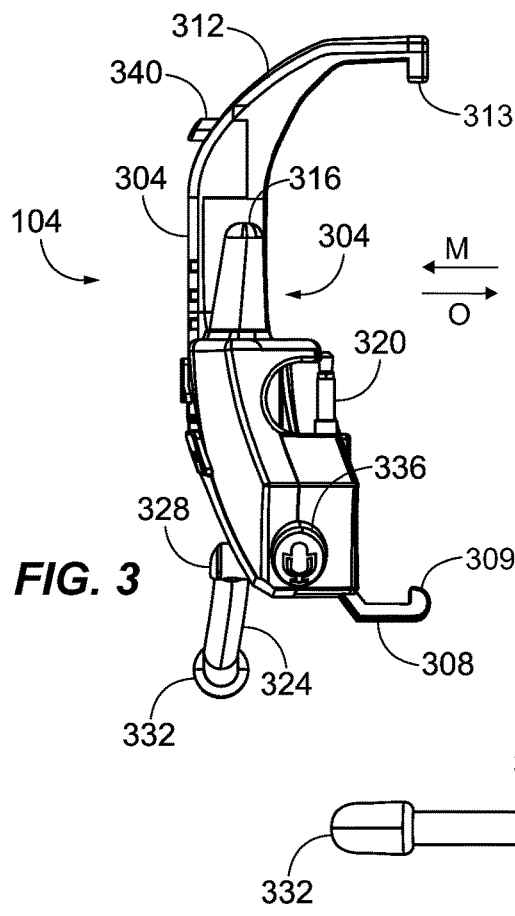
FIG. 3 is a side view of an exemplary communication device.
Figure 4:
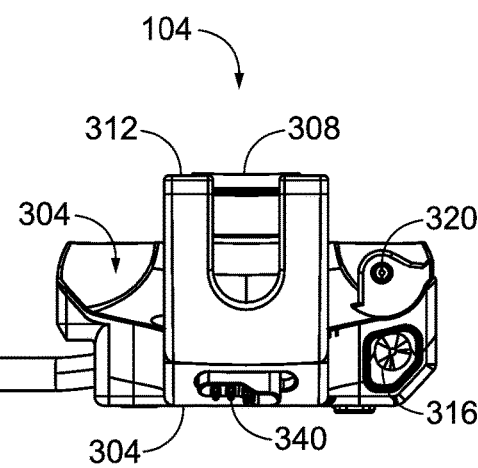
FIG. 4 is a top view of an exemplary communication device.

FIGS. 3 and 4 respectively illustrate side a top views of an exemplary communication device 104 and components thereof. A communication device 104 may comprise a housing or enclosure 304 that houses or supports various components of the communication device. An enclosure 304 will typically also facilitate removable attachment to a hearing protection device.

For instance, a communication device 104 may comprise one or more device mounts 308, 312 for removably attaching the communication device to a hearing protection device. As can be seen from FIG. 3, a device mount 308, 312 may be shaped to engage a hearing protection device to attach a communication device 104 thereto. In the embodiment of FIG. 3, for instance, the device mounts 308, 312 extend rearward from the enclosure 304 and comprise a projection 309, 313 at their distal ends that engage a cup of a hearing protection device.

A device mount 308, 312 may be a hook or hook shaped, like that shown, or may comprise other structures that facilitate removable attachment to a hearing protection device in one or more embodiments. It is noted that a device mount 308, 312 may be formed of a flexible or resilient material to aid in attachment to and removal from a hearing protection device, while an enclosure 304 remains rigid or at least more rigidly formed. One or more fasteners, such as screws, pins, or the like may be used to secure a communication device 104 in one or more embodiments.

As shown, a first device mount 308 is at a one end of the enclosure 304 while a second device mount is at an opposite end. Specifically, in the embodiment of FIG. 3, the first device mount 308 is at the bottom of the communication device 104 while the second device mount 312 is at the top. In such embodiments, one or more device mounts 308, 312 may engage a peripheral area of a cup to attach a communication device 104 thereto.

In some embodiments, an enclosure 304 may be shaped to receive a cup of a hearing protection device, such as to help secure a communication device 104. A back end of an enclosure 304 may have an arcuate shape, such as to correspond to and receive a cup therein. As shown in FIG. 3 for instance, the back end of the enclosure has a concave shape.

One or more audio output connectors 320 will typically extend outward from an enclosure 304. The audio output connector 320 may provide an electrical, optical, or other type of physical connection through which signals may be transmitted to (or received from) a hearing protection device. In the exemplary embodiment of FIGS. 3 and 4, the audio output connector 320 comprises an electrical connector for communicating audio (or other) signals from the communication device 104 to a hearing protection device.

In one or more embodiments, an enclosure 304 and audio output connector 320 operate in conjunction to automatically connect to a hearing protection device when a communication device 104 is attached to the hearing protection device. Referring to FIG. 3, it can be seen that the enclosure 304 supports the audio output connector 320 at a particular location. This location is selected to align with a corresponding connector of a hearing protection device. In this case, the audio output connector 320 extends upright from a platform at a back end of the enclosure. When attached to a cup, the audio output connector 320 is automatically inserted into the corresponding connector at the cup, thereby allowing communication of audio signals therebetween.

A communication device will typically include one or more recording devices, such as one or more microphones 332 to receive a user's voice or other audio. A microphone 332 may be mounted to an enclosure 304. In one or more embodiments, a boom or arm 324 may be provided to position the microphone 332 adjacent a user's mouth or otherwise at a position where the desired audio can be recorded. It is contemplated that a microphone 332 may be movable, such as via mounting on a pivot 328. An arm 324 may also or alternatively be bendable in some embodiments.

One or more antennas 316 will also be typically provided. An antenna 316 aids in transmission and reception of wireless signals to allow communication between multiple communication devices 104. Though shown as a particular antenna 316, it is contemplated that a variety of antennas 316, including internal antennas may be provided. In addition, it is contemplated that one or more antennas 316 may be connected to a communication device 104 via a cable. In this manner, an antenna 316 can be mounted to a hearing protection device or elsewhere, such as to improve signal transmission or reception.

Figure 5:
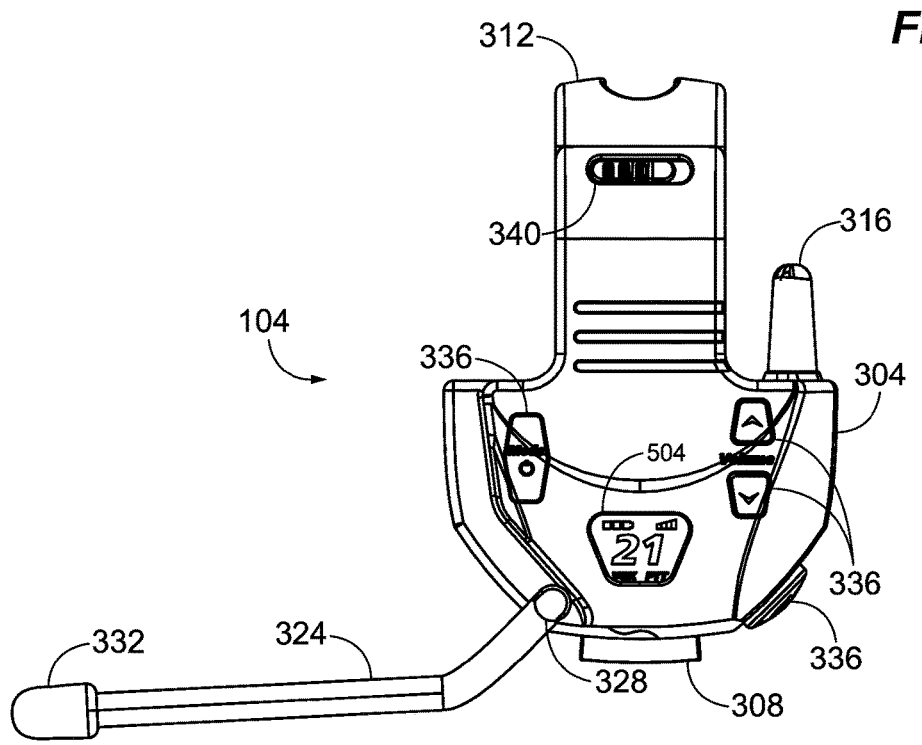
FIG. 5 is a front view of an exemplary communication device.

One or more input devices 336 may be provided to receive user input. To illustrate, an input device 336 may be a button, switch, knob, touch screen, or other user input device. An input device 336 will typically be associated with a particular function. For example, as shown, an input device in the form of a switch 340 is provided to turn the communication device 104 on and off. With reference to FIG. 5, which illustrates a front view of a communication device 104, a plurality of input devices 336 are provided to change channels, raise or lower volume, or activate a push to talk function.

One or more output devices 504 may be provided as well. An output device 504 generally provides feedback to a user. Some exemplary output devices 504 include display screens, vibrators, and speakers for instance. As shown in FIG. 5, the output device 504 comprises a screen that displays battery levels, volume information, and the current communications channel.

FIGS. 6 and 7 illustrate attachment and removal of a communication device 104 relative to a hearing protection device 108. As shown in FIG. 6, one or more device mounts 312 may be removable to facilitate such attachment and removal.

For example, to attach a communication device 104, a first device mount 312 may first be removed, as shown in FIG. 6. The back end of the enclosure 304 may then receive or engage a portion of the hearing protection device 108, such as a cup 116 of the hearing protection device, with a second device mount 308 engaging a structure thereof, such as a lip, edge, or other portion of the cup. The first device mount 312 may then be reattached to the enclosure 304 while engaging the cup as well.

The communication device 104 is attached to the hearing protection device 108 in this manner, as shown in FIG. 7. As can be seen, a projection or hook 309, 313 of the device mounts 308, 312 engage the cup 116 in a transverse direction T, being transverse to a mounting direction M, to secure the communication device 104 thereto. As disclosed above, the attachment operation also connects an audio output connector of the communications device 104 to the hearing protection device 108. In this state, the communication device 104 may be considered ready for use.

A device mount 312 may be made removable in various ways. Referring to FIG. 6, a device mount 312 may be removable in a direction T, being transverse to a mounting direction M, via a tab or member 604 that is received within a corresponding groove, slot, or compartment 608. It is contemplated that various combinations of mating structures may be provided at the device mount 312 and enclosure 304. In addition, one or more fasteners, such as screws, pins, magnets, or the like, may be used to secure a device mount 312 in a removable fashion. In the embodiment of FIG. 6, a friction fit secures the device mount 312 to the enclosure 304.

Removing a communication device 104 is generally a reverse procedure. In one or more embodiments, for example, one or more device mounts 308, 312 may be disengaged from the hearing protection device 108, and thereafter the communication device 104 may be removed. In the embodiment of FIG. 6, the first device mount 312 may be removed from the enclosure 304, thereby disengaging the first device mount from the hearing protection device's cup 316. Thereafter, the enclosure 304 and the remainder of the communication device 304 can be removed from the hearing protection device 108.

In some embodiments, device mounts 308, 312 need not be removable. As set forth above, a device mount 308, 312 may be flexible or resilient such as to allow malleability during attachment to and removal from a hearing protection device 108. To illustrate, one or more device mounts 308, 312 may be bent or otherwise manipulated when a cup 316 or other portion of a hearing protection device 108 is received or engaged by the enclosure 304 of a communication device 104 in a mounting direction M. A device mount 308, 312 can then be allowed returned to a normal or at rest state to secure a communication device 104 to a hearing protection device 108. Likewise, one or more device mounts 308, 312 can be bent or manipulated to allow a cup 316 to be disengaged from an enclosure 304 when removing the communication device 104 from a hearing protection device 108 in a direction O, being opposite to the mounting direction M. It is contemplated that one or more portions of an enclosure 304 may be formed of a resilient material to aid in attachment and removal as well.

Figure 8:
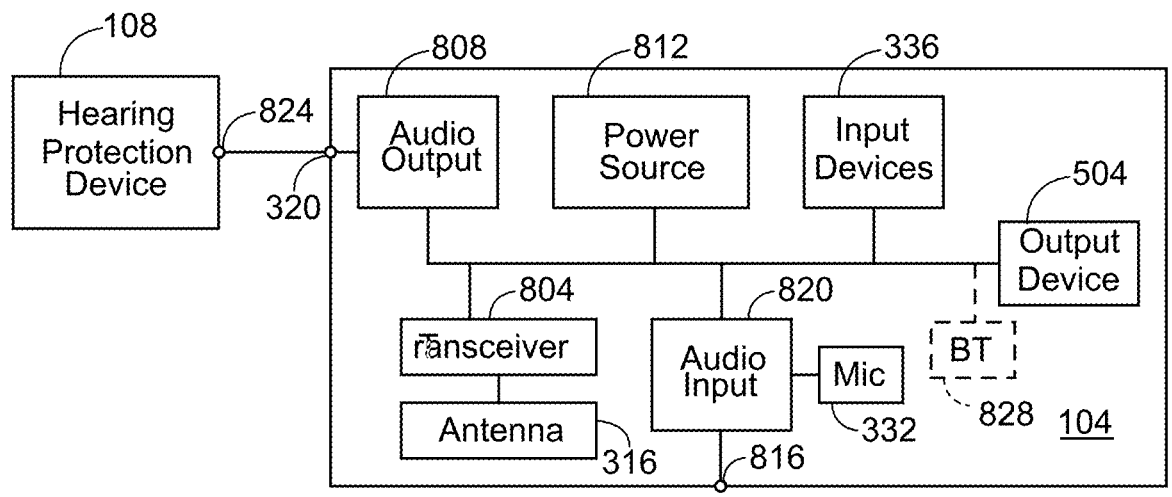
FIG. 8 is a block diagram illustrating components of an exemplary communication device.

FIG. 8 illustrates components of an exemplary communication device 104 that is connected to a hearing protection device 108. Though shown as being connected via a bus, it will be understood that the components may be connected in various ways.

As can be seen, a communication device 104 may comprise one or more radio transceivers 804, one or more power sources 812, one or more audio outputs 808, and one or more audio inputs 820. A power source 812 may comprise one or more batteries, solar panels, generator, or other device that is capable of providing power. A combination of various power sources 812 may be used in some embodiments.

Some power sources 812 may be used to charge other power sources. Typically, a power source 812 will be portable, such as a battery.

A radio transceiver 804 may wirelessly transmit audio or other signals, receive such signals, or both. A radio transceiver 804 will typically be connected to one or more antennas 316 and may be capable of communicating wirelessly via one or more communication channels or frequencies, selectable by a user.

It is contemplated that one or more preset sounds or signals may be transmitted by a communication device 104. For example, prerecorded vocalizations, music, sounds, or the like may be transmitted upon engagement of a particular input device 336. A user may select from several preset sounds or signals in some embodiments, via one or more input devices 336. This provides particular information to other users depending on the transmitted sounds or signals, and may be used for entertainment purposes as well. The preset sounds or signals may be recorded or stored on a storage device that is part of or connected to a radio transceiver 804.

Though disclosed above as a radio transceiver 804 capable of transmitting and receiving, it is contemplated that in some embodiments, only a radio transmitter or radio receiver may be provided for one-way or broadcast communication between communication devices 104. In addition, it is contemplated that communication devices 104 need not communicate via radiofrequency transmissions in the various embodiments of the invention. For example, a communication device 104 may communicate optically via lasers, infrared, or other light signals in some embodiments. Accordingly, a variety of transceivers, including optical transceivers, may be utilized.

As disclosed above, a user's vocalizations and other local sounds may be received at an audio input 820. An audio input 820 will generally convert audio or sound into electrical signals, and may receive such audio from one or more microphones 332. An audio input 820 may also or alternatively receive audio from another source via an audio input connector 816.

For example, one or more independent microphones, or the audio output of another device may be connected via an audio input connector 816. A user may play music for instance through a smartphone or portable media player connected to the audio input connector 816. An audio input connector 816 may be an electrical, optical, or other connector. One or more cables may be used to connect external devices to an audio input connector 816.

The audio received at an audio input 820 will typically be transmitted to a radio transceiver 804 for transmission to other communication device 104. This may occur in an automated fashion or when a user engages a push to talk button input device 336 or the like. The same audio may optionally also be outputted via an audio output 808 so that a user can ultimately hear what is being captured or transmitted by their communication device 104.

An audio output 808 generally provides a signal, such as an electrical or optical signal, that can then be outputted to a user in audible form. Typically, an audio output 808 will receive at least the transmissions from a radio transceiver 804. These transmissions include remote audio, which is the transmitted audio from the communication devices 104 of other users. The audio output 808 then provides a corresponding signal to this remote audio as output.

As shown in FIG. 8, this output is received at a hearing protection device 108, when the hearing protection device is connected to the communication device 104. As disclosed above, the connection with a hearing protection device 108 may occur via one or more audio output connectors 320 of the communication device 104 that connect to a corresponding connector 824 of the hearing protection device.

It is contemplated that a length of cable (not shown) between an audio output connector 320 and an audio output 808 may be provided in some embodiments. This allows a communication device 104 to connect to a wide variety of hearing protection devices 108. It is contemplated that such cable (not shown) may be retractable in some embodiments.

Though described as an audio input 816 or audio output 808, it is contemplated that either component or both components may function as an input and output device for audio or other signals. For example, control signals for controlling volume or other functionality may be transmitted or received via an audio input 816 or audio output 808. Also, accordingly, an audio input and output may be a single combined component in some embodiments.

It is also contemplated that various wireless connections may be used in addition or instead of the audio input connectors 816 and audio output connectors 320 disclosed above. For example, a BLUETOOTH transceiver or other short-range wireless transceiver 828 may be provided to transmit and receive audio signals. In such embodiments, an audio input 820, audio output 808, or both may be connected to a short-range wireless transceiver 828 thereby reducing or eliminating the need for physical connections with a hearing protection device 108, external microphone, smartphone, or other external device.

As disclosed above, an output device 504 may present communication device status or configuration information, such as battery levels, volume, channel or frequency information, and other information.

Figure 9:
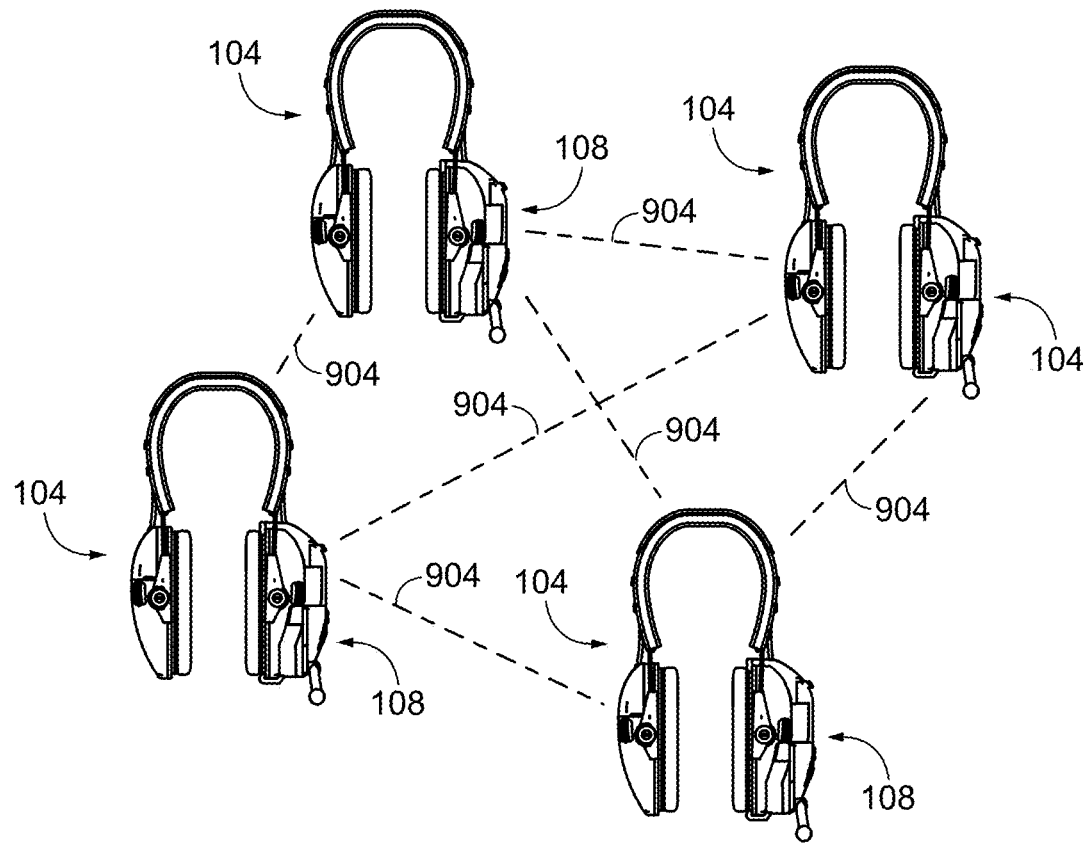
FIG. 9 illustrates exemplary communication devices in operation.

FIG. 9 illustrates a plurality of communication devices 104 in use. As can be seen, each communication device 104 has been attached to a hearing protection device 108. Accordingly, the corresponding users have their hearing protected via active attenuation provided by their hearing protection device 108. This is beneficial in reducing or eliminating the likelihood of hearing damage caused by firearm discharge, industrial noise, or other high decibel sounds. However, the ability for the users to communicate amongst one another is not limited. Instead, the users' ability to communicate is enhanced via the communication devices 104 attached to their hearing protection devices 108. Namely, each user can now communicate wirelessly (904) across a distance while being audible despite the adornment of hearing protection devices by their peers.

As each user speaks, their voice is captured and transmitted from their communication device 104 to other communication devices. The receiving communication devices 104 output the user's voice via a speaker of the attached hearing protection device 108. While the hearing protection device 108 is actively attenuating harmful sounds, the output of a communication device 104 is passed through, allowing the same to be heard clearly. It is contemplated that, in some embodiments, an audio output 808 may change or alter the pitch, volume, or other characteristic of audio such that it is not attenuated by a user's particular hearing protection device 108.

As can be seen, the communication device 104 is highly beneficial to users that desire or require hearing protection and the ability to communicate easily without hinderance. This is quite often in hunting, shooting, industrial, or other environments with undesirable sound or noise levels.

Figure 10:
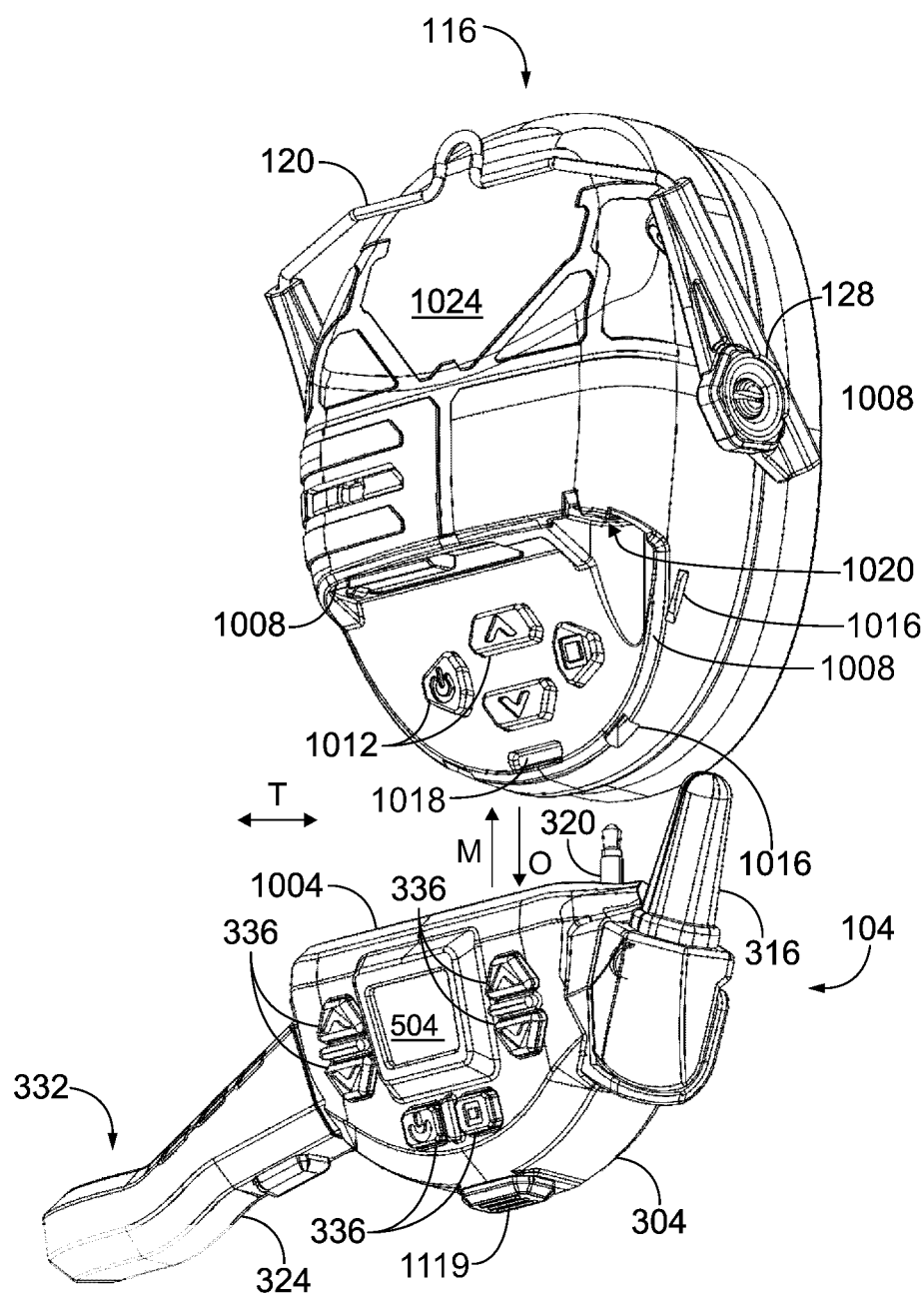
FIG. 10 is a front perspective view of an exemplary communication device and cup.

FIG. 10 illustrates another exemplary communication device 104 that may be removably secured to a hearing protection device. In FIG. 10, the communication device 104 is shown disengaged from a cup 116 of a hearing protection device.

Similar to above, the communication device 104 of FIG. 10 comprises one or more microphones 332, input devices 336, output devices 504, and connectors 320 housed or otherwise supported by an enclosure 304. An antenna 316 may be provided to facilitate wireless communication.

Also similar to above, a cup 116 may comprise an arm 120 and pivoting mount 128 for securing the cup to a hearing protection device. A cup 116 may comprise one or more input devices 1012 such as for independently controlling the operation of the hearing protection device. Various ports 1020 may be provided for connecting a cup 116 to a connector 320 of a communication device 104 for communication purposes. For example, input from one or more input devices 336 of a communication device 104 may be transmitted to a hearing protection device through a connector 320 and port 1020, such as to allow such input to control aspects of the hearing protection device's operation.

Figure 11:
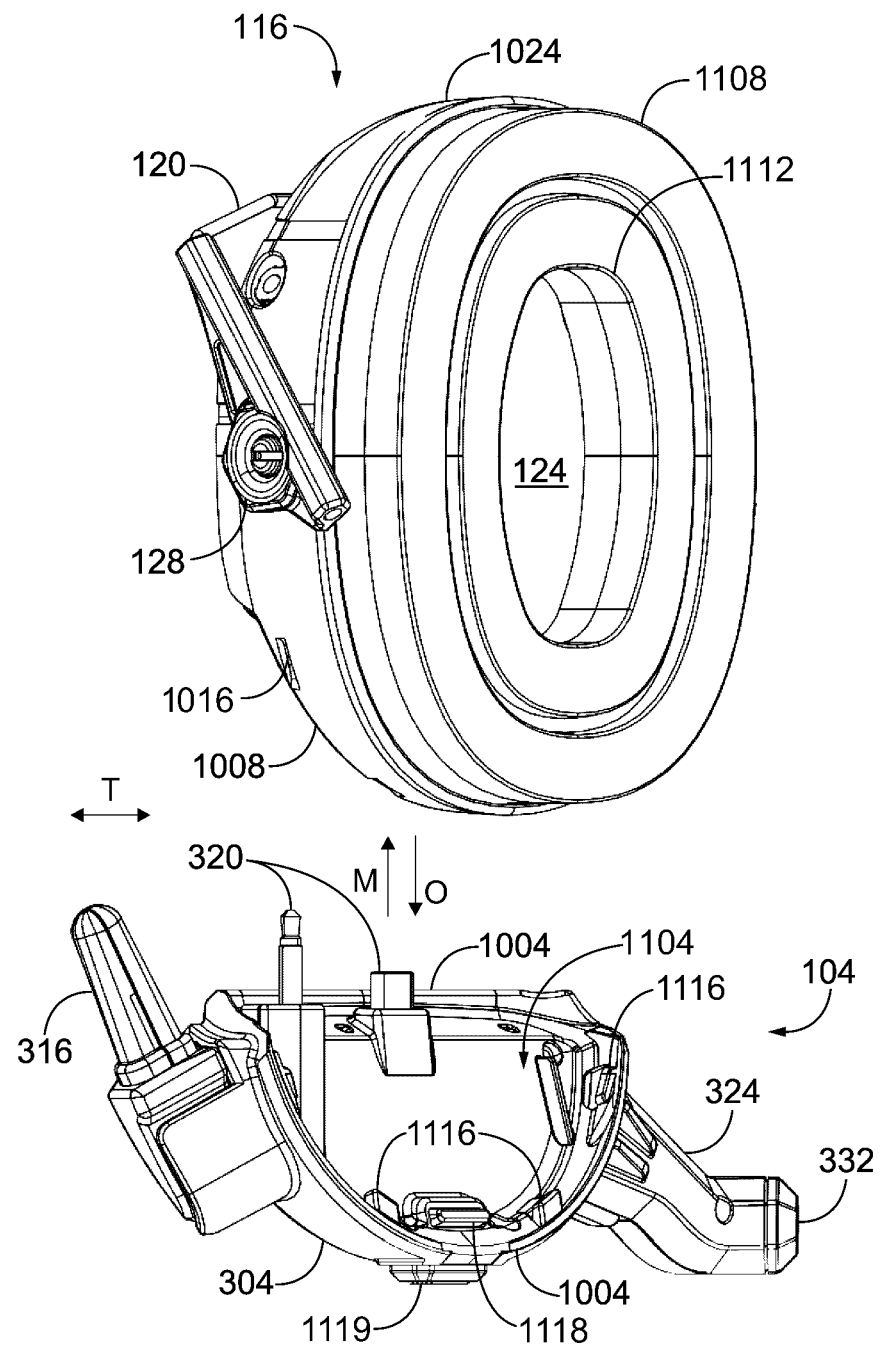
FIG. 11 is a back perspective view of an exemplary communication device and cup.

A cup's enclosure 1024 will typically house or otherwise support various components of a cup 116 such as the previously described input devices 1012 and ports 1020. It is noted that a cup 116 may, in one or more embodiments, comprise a plurality of seals 1108, 1112 to provide enhanced hearing protection. As shown in FIG. 11 for instance, the cup 116 comprises concentric seals 1108, 1112 to provide enhanced hearing protection.

A communication device 104 may be removably secured to a hearing protection device in various ways. As described above, an enclosure 304 of a communication device 104 may be shaped to receive a cup 116 such as to allow the cup to nest within the communication device's enclosure. As can be seen from FIGS. 11 and 12 (and FIG. 7 above), an enclosure 304 may have an open portion at its back end that receives a cup 116 therein when the communication device 104 is secured to the cup. A compartment 1104 may be provided to receive a cup 116 in one or more embodiments.

Referring back to FIG. 10, an enclosure 304 of a communication device 104 may comprise one or more mating surfaces 1004. A mating surface 1004 of a communication device 104 may be an edge or other structure that engages a portion of a cup 116, such as at the cup's enclosure 1024. A mating surface 1004 of a communication device 104 may correspond in shape to a portion of a cup 116. In this manner, one or more mating surfaces 1004 may form a friction fit or "click" fit to secure a communication device 104 to a cup 116, such as when the enclosure 304 receives the cup 116.

A cup 116 may also have one or more mating surfaces 1008 that facilitate attachment of a communication device 104. A mating surface 1008 of a cup 116 may be an edge or other structure that engages a communication device 104, such as at the communication device's enclosure 304. A mating surface 1008 may be shaped to correspond to that of a cup's enclosure 304, or portion thereof, to engage and secure the communication device 104 to the cup.

Figure 12:
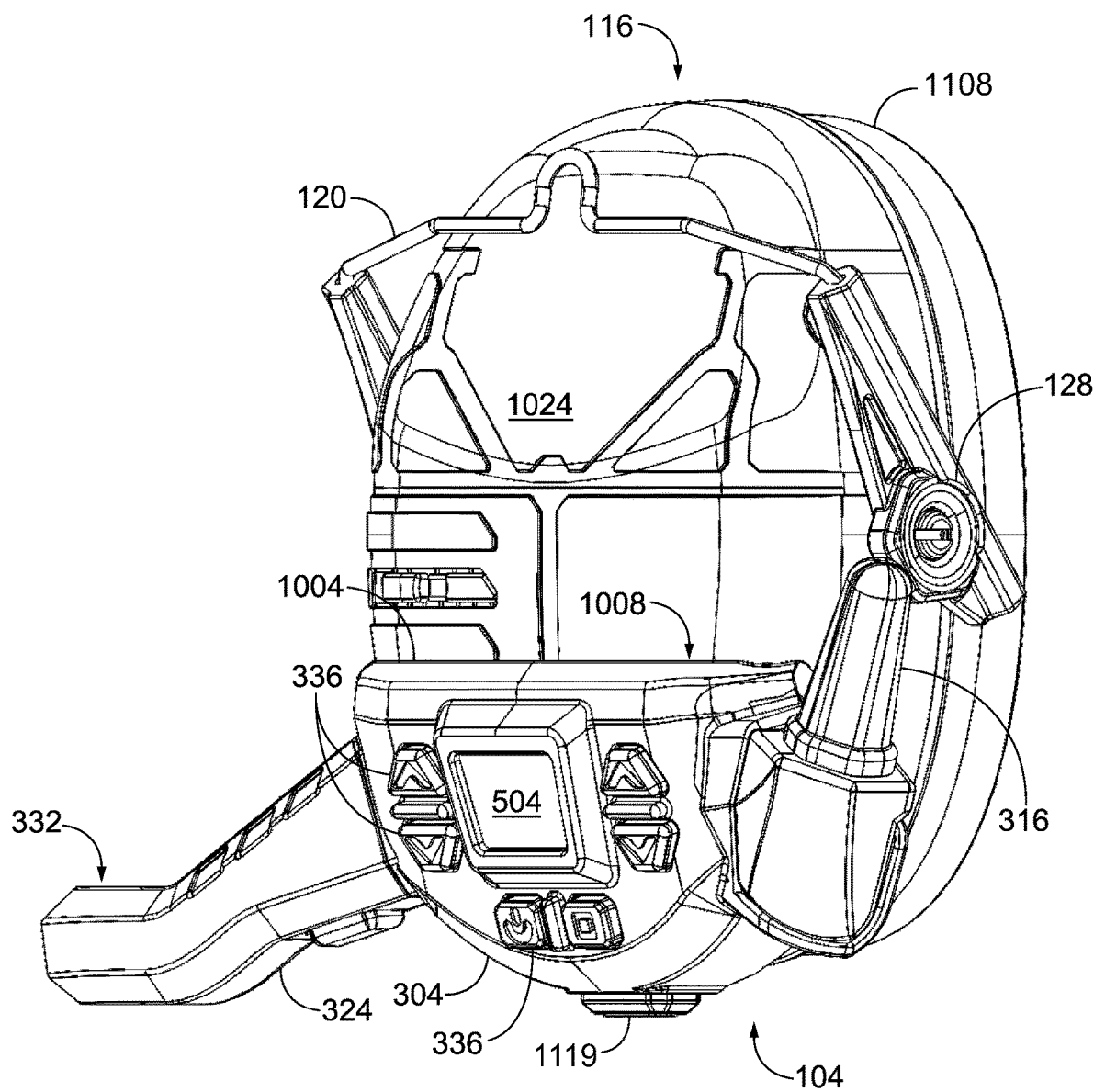
FIG. 12 is a perspective view of an exemplary communication device attached to a cup.

As can be seen in FIG. 12, mating surfaces 1004, 1008 may have corresponding contours and engage one another to secure a communication device 104. In addition, a mating surface 1004 of a communication device 104 may also surround a correspondingly shaped portion of the cup 116. Referring to FIGS. 10 and 11, one or more slots 1016 and 1018, tabs 1116 and 1118, or other fasteners may also be provided to secure a communication device 104 when such fasteners are engaged to one another. One such slot 1016 as shown in FIG. 10 can be provided on the cup 116 and can allow a tab 1116 as shown in FIG. 11 extending on the communication device 104 to be inserted therein/connected thereto when engaging the enclosure 304 with the cup 116 in a mounting direction M and to be removed therefrom/disconnected therefrom when disengaging the enclosure 304 with the cup 116 in the opposite direction O to the mounting direction M.

Another slot 1018 as shown in FIG. 10 can be provided on the cup 116 and can be engaged by a tab 1118 as shown in FIG. 11 provided on the communication device 104. This tab 1118 extends in a direction T, being transverse to the mounting direction M, to engage in the slot 1018 when forming a "click" fit to secure the communication device 104 to the cup 116, such as when the enclosure 304 mounts on the cup 116 in the mounting direction M. A button 1119 on the enclosure 304 can disengage the tab 1018 from the slot 1018 so the enclosure 304 can be removed from the cup 116 in the opposite direction O to the mounting direction D.

While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement.

What is claimed is:

1. A communication device for use with a hearing protection device, the hearing protection device having a cup and an audio input, the cup having an inner side and an outer side, the outer side having first and second portions, the inner side having a speaker in communication with the audio input, the communication device comprising:
   an enclosure having a mounting side, a microphone, a transceiver, and an audio output, the mounting side being configured to position adjacent to the outer side of the cup, the microphone being configured to capture audio, the audio output being configured to connect to the audio input of the hearing protection device, the transceiver in communication with the microphone and the audio output and being configured to wirelessly transmit and receive wireless signals;
   a first mount extending from the mounting side of the enclosure, the first mount being configured to mount to the first portion of the cup in a first removable attachment; and
   a second mount extending from the mounting side of the enclosure, the second mount being configured to mount to the second portion of the cup in a second removable attachment, at least a portion of the second mount being manipulatable relative to the enclosure and being configured to removably engage and disengage with the second portion of the cup.

2. The communication device of claim 1, wherein the first mount comprises a first arm disposed toward a first device end of the enclosure; and wherein the second mount comprises a second arm disposed toward a second device end of the enclosure.

3. The communication device of claim 2, wherein the first arm is configured to engage the cup toward a first cup end of the cup as the first portion; and wherein the second arm is configured to engage the cup toward a second cup end of the cup as the second portion, the second cup end opposing the first cup end.

4. The communication device of claim 2, wherein the first and second arms each comprises a projection configured to engage the cup in the respective first and second removable attachment.

5. The communication device of claim 1, wherein the second mount comprises an arm extending from the mounting side of the enclosure; and wherein the at least the portion of the second mount that is manipulatable comprises the at least a portion of the arm that is flexible, bendable, resilient, or malleable relative to the enclosure.

6. The communication device of claim 1, wherein the second mount comprises an arm extending from the mounting side of the enclosure; and wherein the at least the portion of the second mount that is manipulatable comprises the at least a portion of the arm having a rest state and a bent state, the at least the portion of the arm in the rest state being configured to engage with the second portion of the cup, the at least the portion of the arm in the bent state being configured to disengage with the second portion of the cup.

7. The communication device of claim 1, wherein the second mount comprises an arm; wherein the enclosure defines a compartment; and wherein a portion of the arm is configured to removably fit in the compartment on the enclosure, whereby the arm is attachable on the enclosure to extend from the mounting side of the enclosure and to engage with the second portion of the cup, and whereby the arm is detachable from the enclosure to disengage with the second portion of the cup.

8. The communication device of claim 1, wherein the at least the portion of the second mount, which is manipulatable, comprises a tab extending from the mounting side of the enclosure, the tab being configured to removably engage and disengage with a slot on the second portion of the cup.

9. The communication device of claim 8, wherein the mounting side of the enclosure is configured to position in a mounting direction adjacent to the outer side of the cup, the tab being configured to removably engage and disengage with the slot in a transverse direction, being transverse to the mounting direction.

10. The communication device of claim 8, wherein the tab is configured to engage in a click fit with the slot.

11. The communication device of claim 8, wherein the enclosure comprises a button configured to move the tab to at least removably disengage with the slot.

12. The communication device of claim 8, wherein the second mount comprises another tab extending from the mounting side of the enclosure, the other tab being configured to removably insert into and out of another slot on the first portion of the cup.

13. The communication device of claim 12, wherein the mounting side of the enclosure is configured to position in a mounting direction adjacent to the outer side of the cup, the other tab being configured to removably insert into the other slot in the mounting direction and being configured to removably insert out of the other slot in an opposite direction, being opposite to the mounting direction.

14. The communication device of claim 1, wherein the mounting side of the enclosure defines a first mating surface configured to mate with a second mating surface defined on the outer side of the cup, whereby an external surface of the enclosure completes the outer side of the cup.

15. The communication device of claim 1, wherein the mounting side of the enclosure defines a compartment in which a section of the outer side of the cup positions.

16. The communication device of claim 1, further comprising a connector disposed on the mounting side of the enclosure and being configured to connect to the hearing protection device when the mounting side of the enclosure is positioned adjacent to the outer side of the cup, the connector being configured to communicate one or more signals other than audio signals between the communication device and the hearing protection device.

17. An assembly comprising:
an earmuff having a headband, a cup, and an audio input, the cup having an inner side and an outer side, the outer side having first and second portions, the inner side having a speaker in communication with the audio input; and
a communication device according to claim 1 configured to be removably engaged with the cup.

18. The communication device of claim 1, wherein the second mount comprises an arm extending from the mounting side of the enclosure; and wherein the at least the portion of the arm, which is manipulatable, is resilient such that the arm is configured to pivot away from the second portion of the cup under an applied force and is configured to recoil back toward the second portion when the force is no longer applied.

19. The communication device of claim 1, wherein the second mount comprises an arm extending from the mounting side of the enclosure; and wherein the at least the portion of the arm, which is manipulatable, comprises a rest state and a manipulated state, the at least the portion of the arm in the rest state being configured to engage with the second portion of the cup under a recoil force, the at least the portion of the arm in the manipulated state being configured to disengage with the second portion of the cup under an applied force greater than the recoil force.

20. A communication device for use with a hearing protection device, the hearing protection device having a cup and an audio input, the cup having an inner side and an outer side, the outer side having first and second portions, the inner side having a speaker in communication with the audio input, the communication device comprising:
an enclosure having a mounting side, a microphone, a transceiver, and an audio output, the mounting side being configured to position adjacent to the outer side of the cup in a mounting direction, the microphone being configured to capture audio, the audio output being configured to connect to the audio input of the hearing protection device, the transceiver in communication with the microphone and the audio output and being configured to wirelessly transmit and receive wireless signals;
a first arm disposed toward a first end of the enclosure and extending in the mounting direction from the mounting side, the first arm being configured to mount to the first portion of the outer side of the cup in a first removable attachment; and
a second arm disposed toward a second end of the enclosure and extending in the mounting direction from the mounting side, the second arm being configured to mount to the second portion of the outer side of the cup in a second removable attachment, at least a portion of the second arm being manipulatable relative to the enclosure and being configured to removably engage and disengage the second portion of the cup.

21. The communication device of claim 20, wherein the at least the portion of the second arm, which is manipulatable, is flexible, bendable, resilient, or malleable in a transverse direction, being transverse to the mounting direction.

22. The communication device of claim 20, wherein the at least the portion of the second arm, which is manipulatable, comprises a rest state and a bent state, the at least the portion of the second arm in the rest state being configured to engage with the second portion of the cup, the at least the portion of the second arm in the bent state being configured to disengage with the second portion of the cup.

23. The communication device of claim 22, wherein the first and second arms each comprise a projection configured to respectively engage the first and second portions of the cup in the respective first and second removable attachment.

24. The communication device of claim 20, wherein the enclosure defines a compartment in a transverse direction, being transverse to the mounting direction; wherein a portion of the second arm is configured to removably fit in the compartment on the enclosure; and whereby the second arm is attachable on the enclosure to engage with the second portion of the cup and is detachable from the enclosure to disengage with the second portion of the cup.

25. The communication device of claim 20, wherein the first arm is disposed toward a bottom as the first end of the enclosure; and wherein the second arm is disposed toward a top as the second end of the enclosure.

26. A communication device for use with a hearing protection device, the hearing protection device having a cup and an audio input, the cup having an inner side and an outer side, the outer side having first and second portions, the inner side having a speaker in communication with the audio input, the communication device comprising:

an enclosure having a mounting side, a microphone, a transceiver, and an audio output, the mounting side being configured to position adjacent to the outer side of the cup in a mounting direction, the microphone being configured to capture audio, the audio output being configured to connect to the audio input of the hearing protection device, the transceiver in communication with the microphone and the audio output and being configured to wirelessly transmit and receive wireless signals;

a first tab extending in the mounting direction from the mounting side of the enclosure and being configured to mount to the first portion of the outer side of the cup in a first removable attachment, the first tab being configured to removably insert in the mounting direction into the first portion of the cup and being configured to removably withdraw in an opposite direction, opposite to the mounting direction, from the first portion; and a second tab extending in a transverse direction, being transverse to the mounting direction, from the mounting side and being configured to mount to the second portion of the outer side of the cup in a second removable attachment, the second tab being manipulatable to removably engage and disengage in the transverse direction with the second portion of the cup.

27. The communication device of claim 26, wherein the second tab is configured to engage with a click fit with the second portion of the outer side of the cup.

28. The communication device of claim 26, wherein the enclosure comprises a button configured to move the second tab to at least removably disengage with the second portion.

* * * * *